United States Patent [19]

Newman et al.

[11] 4,173,074
[45] Nov. 6, 1979

[54] HAND MEASURING DEVICE

[75] Inventors: Howard F. Newman, Los Angeles; Benjamin Stansbury, Beverly Hills, both of Calif.

[73] Assignee: American Hospital Supply Corporation, Evanston, Ill.

[21] Appl. No.: 846,924

[22] Filed: Oct. 31, 1977

[51] Int. Cl.$^2$ .............................................. A41H 1/02
[52] U.S. Cl. .................................... 33/2 R; 33/174 D
[58] Field of Search ............................. 33/2 R, 174 D

[56] References Cited
U.S. PATENT DOCUMENTS

| 1,261,459 | 4/1918 | Thalimer | 33/3 B |
| 1,324,267 | 12/1919 | Pietzuch | 33/3 B |
| 1,725,334 | 8/1929 | Brannock | 33/3 B |
| 2,018,630 | 10/1935 | Bliss | 33/3 B |
| 2,605,548 | 8/1952 | Clarke | 33/2 R |

Primary Examiner—Willis Little
Attorney, Agent, or Firm—Larry N. Barger

[57] ABSTRACT

A device for measuring a hand which is particularly useful for a surgeon in selecting a particular size of latex surgeon's glove. The device has structure for measuring the length of a finger and coordinating it with a width of a palm of the hand to select a glove size.

4 Claims, 4 Drawing Figures

HAND MEASURING DEVICE

BACKGROUND OF THE INVENTION

Even though a latex surgeon's glove is highly stretchable, it is important that the surgeon have a proper fit for tactile sensitivity and ease of hand movement.

An improved surgeon's glove and how it is sized is described in detail in the following two co-pending patent applications by Benjamin Stansbury:

Highly Stretchable Glove and Form for Making Same, Ser. No. 846,911, Filed Oct. 31, 1977, now abondoned.

Highly Stretchable Gloves and Method of Sizing Same, Ser. No. 846,928, Filed Oct. 31, 1977, now U.S. Pat. No. 4,115,873.

SUMMARY OF THE INVENTION

The present invention is a device for measuring a surgeon's hand so that he can properly select the proper size of surgeon's gloves in a size distribution as described in the above two applications. The hand measuring device has a structure for coordinating the length of one finger, such as a middle finger, with a palm width to establish a proper glove size.

THE DRAWINGS

DETAILED DESCRIPTION

Figure 1:
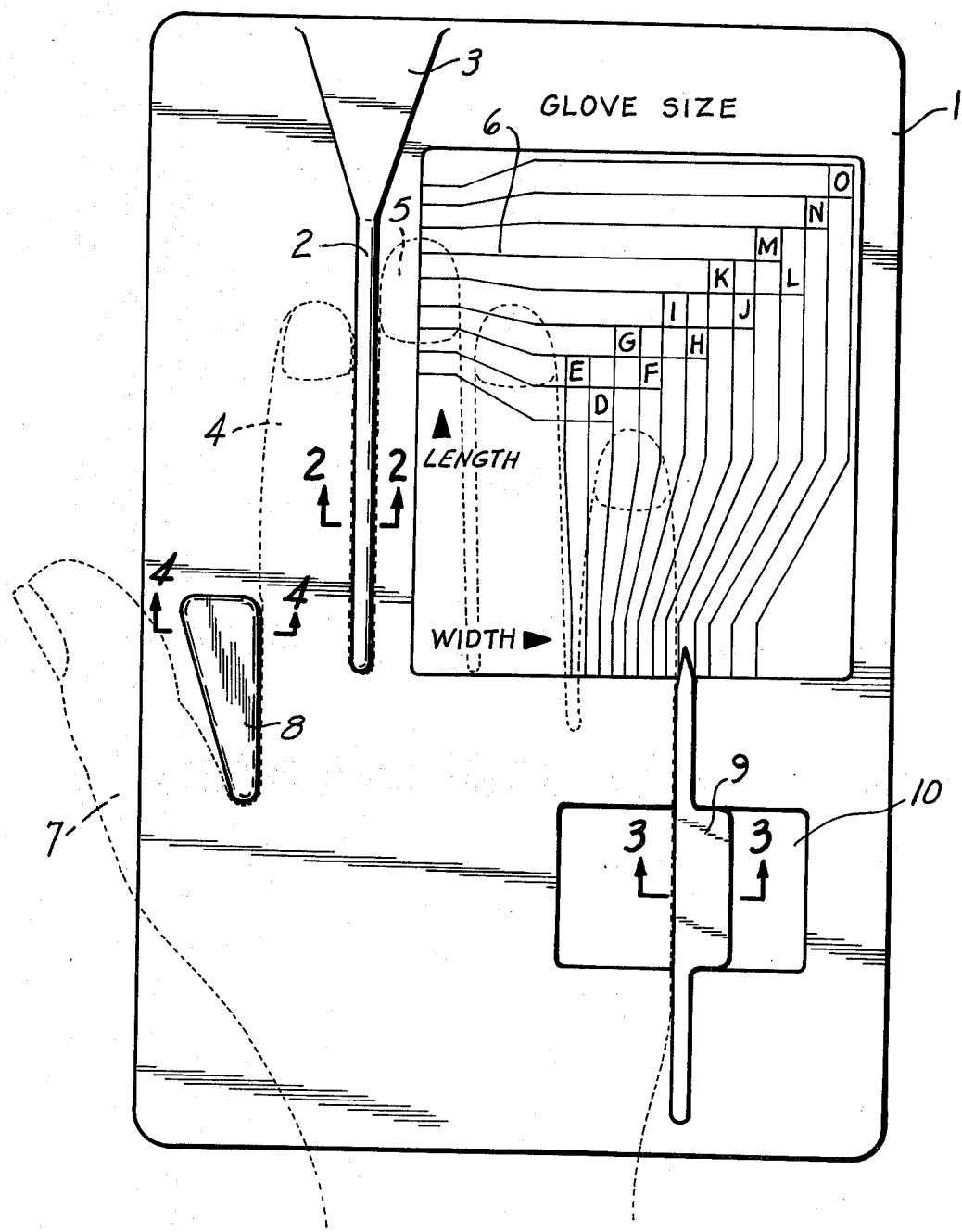
FIG. 1 is a top plan view of the hand measuring device.
Figure 2:
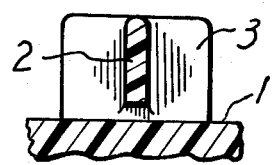
FIG. 2 is a sectional view taken along line 2—2 of FIG. 1.
Figure 3:
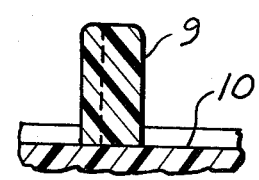
FIG. 3 is a sectional view taken along line 3—3 of FIG. 1.
Figure 4:
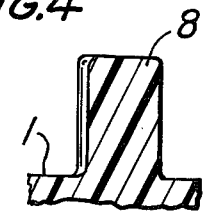
FIG. 4 is a sectional view taken along line 4—4 of FIG. 1.

In FIG. 1 a supporting base 1 has secured thereto a longitudinal upstanding finger crotch stop 2. If desired, this finger crotch stop 2 can be anchored at a widened area 3 to the supporting base 1. A section of the crotch stop 2 that sits between fingers 4 and 5 can be spaced slightly from supporting base 1, as shown in FIG. 2, to permit slight lateral movement to accept different hand sizes.

As explained in the two co-pending applications mentioned in the beginning of the specification, it has been determined that finger length and palm width are the two most critical size dimensions in a highly stretchable latex surgeon's glove. With the present hand measuring device the length of middle finger 5 can be measured by a transverse measuring line, such as 6.

Preferably the palm width is measured to determine glove size, and thus thumb 7 is not included in a lateral measurement. To accomplish this, the hand measuring device has a lateral stop 8 that fits against an inside of the palm in an area roughly between the thumb and forefinger. Stop 8 can be permanently fixed to supporting base 1. A laterally moveable gauge member 9 is secured to a panel 10 that can slide in an internal track system (not shown) within the body of supporting base 1. Laterally movable gauge 9 is adapted to engage an outer edge of a palm, thus indicating its lateral width. A pointer is attached to laterally movable gauge 9 and is adapted to indicate the particular glove size. In the example shown in FIG. 1, a surgeon would use a glove size "M". In FIG. 1, the lead lines between the finger length measurement and palm width measurement are spaced further apart in an area where the size indication is printed on the measuring device. This is for improved readability of the sizes, and does not affect the accuracy of the measurements taken along the left side (finger length) and along the bottom (palm width) of the measuring indicia on the device. Also, there is no significant change in finger length measurement due to the slight lateral flexure of finger crotch stop 2 as it moves slightly to the left or right in FIG. 1 to accomodate different thicknesses of index fingers as the palm is abutted against stationary stop 8.

The above structural coordination between the finger length measurement and palm width measurement are given only as examples, and other intersecting structure could be used if desired.

In the foregoing description, a specific example has been used to describe the invention. However, it is understood by those skilled in the art that certain modifications can be made to this example without departing from the spirit and scope of the invention.

We claim:

1. A hand measuring device for use in selecting a surgeon's glove comprising: a supporting base; a lateral stop fixed to the base and having an upstanding portion against which is placed one edge of a hand's palm; and upstanding gauge member connected to the base, said gauge member being laterally movable relative to said lateral stop for contacting an opposite edge of such palm to measure its width; a thin upstanding crotch stop laterally spaced from the lateral stop for positioning between two fingers; said crotch stop being fixed against longitudinal movement relative to the base, but having a finger crotch engaging portion that is laterally movable so as to accept different finger thicknesses between the lateral and crotch stops; means for measuring finger length; and indicator means on the device for correlating the palm width and finger length into a proper glove size reading.

2. A device as set forth in claim 1, wherein the hand width measuring means includes a lateral stop for engaging a hand between thumb and forefinger for measuring a width of the palm without including a thumb width.

3. A device as set forth in claim 1, wherein the device includes structure for visibly indicating both finger length and hand width.

4. A device as set forth in claim 3, wherein the device has indicia of finger length and indicia of hand width that intersect at a glove size marking.

* * * * *